(12) United States Patent
Germouni et al.

(10) Patent No.: US 7,358,860 B2
(45) Date of Patent: Apr. 15, 2008

(54) METHOD AND APPARATUS TO MONITOR AND DETECT CRYOGENIC LIQUEFIED GAS LEAKS

(75) Inventors: Omar Germouni, Chicago, IL (US);
Indrasis Mondal, Chicago, IL (US);
Thomas Parias, Chicago, IL (US);
Charles N. Harper, Houston, TX (US);
Michael T. Boczon, Houston, TX (US);
Joel R. Henry, Pearland, TX (US)

(73) Assignees: American Air Liquide, Inc., Houston, TX (US); Air Liquide Large Industries U.S. LP, Houston, TX (US)

( * ) Notice: Subject to any disclaimer, the term of this patent is extended or adjusted under 35 U.S.C. 154(b) by 213 days.

(21) Appl. No.: 11/375,529

(22) Filed: Mar. 14, 2006

(65) Prior Publication Data

US 2006/0220888 A1    Oct. 5, 2006

Related U.S. Application Data

(60) Provisional application No. 60/666,853, filed on Mar. 31, 2005.

(51) Int. Cl.
*G08B 21/00* (2006.01)
(52) U.S. Cl. .................. 340/605; 340/603; 340/606
(58) Field of Classification Search .............. 340/605
See application file for complete search history.

(56) References Cited

U.S. PATENT DOCUMENTS 3,572,085 A    3/1971    Packo
3,771,350 A    11/1973   Romans
3,967,256 A *  6/1976    Galatis .................. 340/605
5,001,346 A *  3/1991    Barkhoudarian ............ 250/330
5,523,569 A *  6/1996    Hornfeld et al. ............ 250/330

FOREIGN PATENT DOCUMENTS

| EP | 0 229 762 B1 | 6/1986 |
| EP | 0 536 586 A1 | 4/1993 |
| EP | 0 632 259 A3 | 1/1995 |
| EP | 0 632 259 B1 | 1/1995 |
| GB | 917988       | 2/1963 |

* cited by examiner

*Primary Examiner*—Jeffery Hofsass
*Assistant Examiner*—Kerri McNally
(74) *Attorney, Agent, or Firm*—Elwood Haynes

(57) ABSTRACT

Embodiments of the invention provide a method, article of manufacture, and system of detecting a cryogenic leak. In one embodiment, the method includes calibrating an infrared camera by detecting one or more first areas of low temperature in a first infrared image of a location received from the infrared camera wherein the low temperature is lower than an ambient temperature, detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generating an alarm message which indicates the cryogenic leak.

25 Claims, 8 Drawing Sheets

METHOD AND APPARATUS TO MONITOR AND DETECT CRYOGENIC LIQUEFIED GAS LEAKS

CROSS-REFERENCE TO RELATED APPLICATIONS

This application claims the benefit under 35 U.S.C. § 119(e) to provisional application No. 60/666,853, filed Mar. 31, 2005, the entire contents of which are incorporated herein by reference.

BACKGROUND

Many industries such as the steel, oil refining, chemicals, glass, electronics, healthcare, food processing, metallurgy, paper and aerospace industries utilize industrial gases such as oxygen, nitrogen, hydrogen, and synthetic gas (syngas). As such, many plant facilities may be provided to produce such gases. In some cases, the plant facilities may be unmanned. Furthermore, in large manned plant facilities, it may be difficult to monitor every portion of the plant facility e.g., due to the size of the plant facility or due to reduced accessibility to areas in which leaks may occur. Because the plant facilities may be unmanned or difficult to monitor, the operator of the plant facilities may utilize error detection systems to determine if the plant facilities are operating correctly and to dispatch personnel to the plant facility or portion of a plant facility which requires maintenance in response to detecting an error.

As an example, the operator may desire the ability to determine if a cryogenic leak has occurred within a given plant facility. Typically, the gases produced in such a plant facility may be stored and/or maintained at low temperatures (e.g., cryogenic temperatures, far below the freezing point of water, for instance, at or below the freezing point for hydrogen or oxygen). In many cases, such gases may evaporate quickly after leaking, and because cryogenic liquefied gases such as liquid oxygen (LOX) may be present in the natural ambient gas surrounding the plant facility, detection of such a cryogenic leak using gas sensors may be difficult. Often, due to high humidity, a vapor cloud (fog) may develop around cryogenic equipment, resulting in poor visibility by cameras operating only in the visible spectrum, making detection of leaks using cameras operating only in the visible spectrum difficult. Furthermore, the quick evaporation of the cryogenic liquefied gases may also make detection of a cryogenic leak using a temperature sensor difficult.

Accordingly, what is needed is an improved system, article of manufacture, and method for detecting a cryogenic leak.

SUMMARY

Embodiments of the invention provide a method, article of manufacture, and system of detecting a cryogenic leak. In one embodiment, the method includes calibrating an infrared camera by detecting one or more first areas of low temperature in a first infrared image of a location received from the infrared camera wherein the low temperature is lower than an ambient temperature, detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generating an alarm message which indicates the cryogenic leak.

One embodiment of the invention provides a computer-readable medium including a program which, when executed by a processor, performs a method of detecting a cryogenic leak. The method includes calibrating an infrared camera by detecting one or more first areas of low temperature in a first infrared image of a location received from the infrared camera wherein the low temperature is lower than an ambient temperature, detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generating an alarm message which indicates the cryogenic leak.

One embodiment of the invention provides a system including an infrared camera and a processor. The processor is configured to calibrate the infrared camera by detecting one or more first areas of low temperature in a first infrared image of a location received from the infrared camera wherein the low temperature is lower than an ambient temperature, detect one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generate an alarm message which indicates the cryogenic leak.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Embodiments of the invention provide a method, article of manufacture, and system of detecting a cryogenic leak. In one embodiment, the method includes calibrating an infrared camera by detecting one or more first areas of low temperature in a first infrared image of a location received from the infrared camera wherein the low temperature is lower than an ambient temperature, detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generating an alarm message which indicates the cryogenic leak. By using an infrared image to detect a cryogenic leak, image processing and pattern recognition tools may be utilized to achieve accurate and fast alarms, thereby increasing safety and reliability while avoiding production losses.

EXAMPLES

Figure 1:
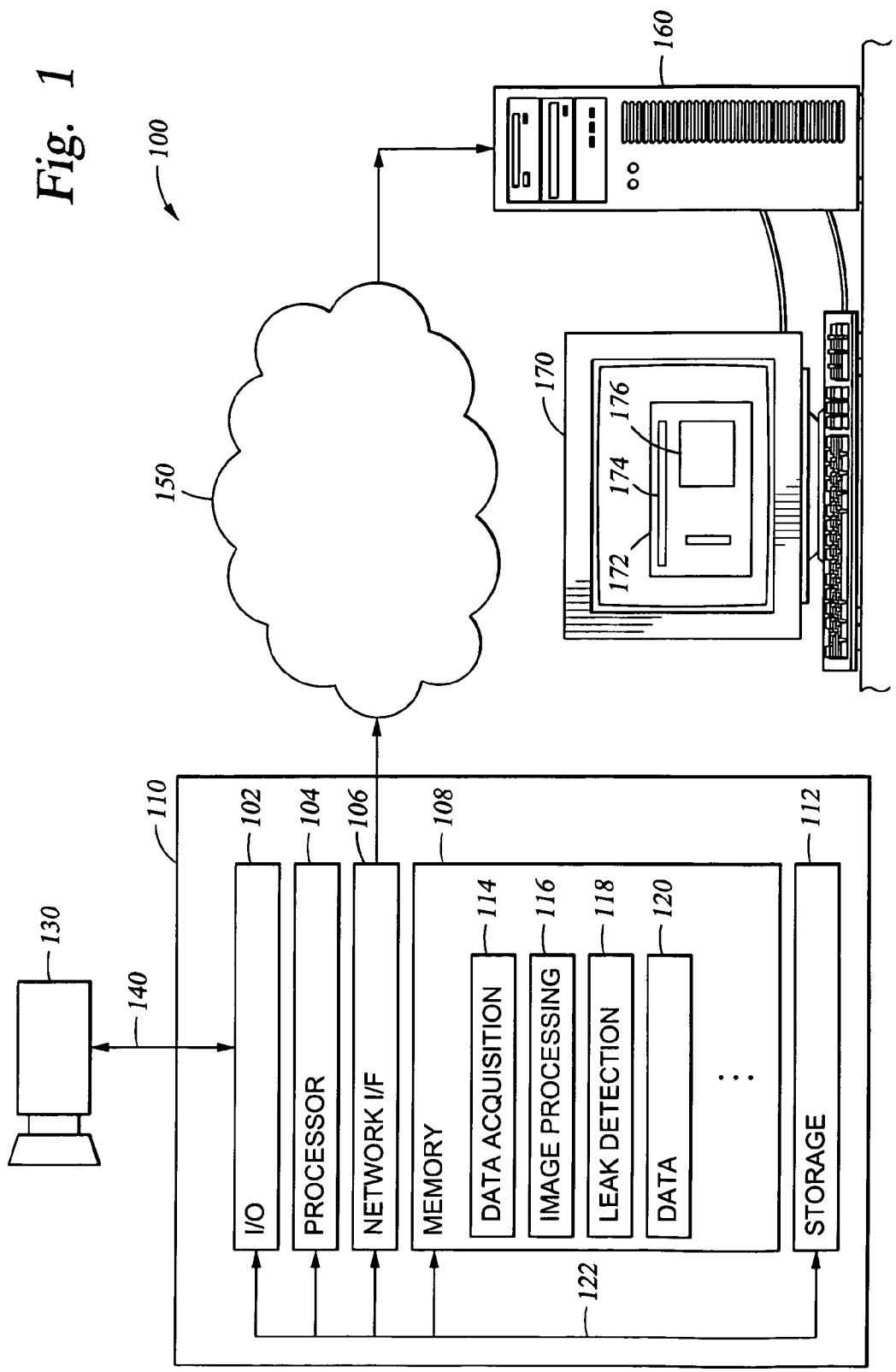
FIG. 1 is a block diagram depicting an exemplary system according to one embodiment of the invention.

FIG. 1 is a block diagram depicting an exemplary system 100 according to one embodiment of the invention. As depicted, the system 100 may include a first computer 110 used for data collection (e.g., a data collection system, DCS), an infrared (I/R) camera 130, a network 150, a second computer 160, and a video display terminal 170 attached to the second computer 160. The I/R camera 130 may be used to take I/R images, e.g., images in which each array component in the image temperature array indicates a detected temperature of an object occupying the corresponding area of the image. Processing in the first computer 110 may be performed by a processor 104. The processor 104 may process programs in a memory 108 including a data acquisition program 114, an image processing program 116, an leak detection program 118. The processor 104 may also process data 120 and other programs or information. Such data and programs may also be stored in a mass storage device 112 such as a hard drive or other computer-readable medium (e.g., a compact disc or read-only memory). Internal components of the first computer 110 may communicate via a data bus 122.

The first computer 110 may utilize an input/output (I/O) interface to request and/or receive I/R images from the I/R camera 130 via a communications link 140. In one embodiment of the invention, the communications link may utilize a USB 1.0 or USB 2.0 communications interface. Optionally, other protocols (e.g., RS-232, IEEE802/3, IEEE1394) may be utilized to communicate with the I/R camera 130. Such images may be acquired using the data acquisition program 114 executed by the processor 104. For example, the processor 104, when executing the data acquisition program 114, may periodically request an I/R image from the camera 140 and download the image via the communications link 140. The downloaded image may then be processed by the image processing program 116. A leak detection program 118 may then determine if the I/R image indicates that a cryogenic leak has been detected.

If a cryogenic leak is detected, the first computer may send an alarm message via a network interface (I/F) 106 across the network 150 to the second computer 160. In response to receiving the alarm message, the second computer 160 may display an alarm notification 172 on the display 170. The alarm notification 172 may include a message 174 indicating the cause, nature and/or location of the alarm (e.g., the message may identify the cause and location of the alarm, for example, "There is a cryogenic leak in the Air Separation Unit at the ABC facility", where ABC may be a town or city) and/or a picture 176 depicting the location of the cryogenic leak and/or the I/R image received from the camera 130. A user of the second computer 160 may then take appropriate action in response to receiving the alarm notification (e.g., the user may notify a repair crew to report to the location of the cryogenic leak).

Optionally, other action may be taken automatically, for example, by the first computer 110 or the second computer 160. For example, the first computer 110 may automatically notify a repair crew or other appropriate personnel by sending additional alarm messages, for example, via email or voicemail. In some cases, such alarm messages may be received on mobile devices such as a personal data assistant (PDA) with internet connectivity and/or a cell phone. Furthermore, in response to detecting a cryogenic leak, the first computer 110 and/or second computer 160 may automatically close a shut-off valve, thereby cutting off gas pressure in the area of the plant in which the cryogenic leak occurs. Optionally, an interface may be displayed, for example, to a user of the second computer 160 which depicts the cryogenic leak and provides the user with an option to take appropriate action such as closing the shut-off valve.

While described above with respect to a first computer 110 and a second computer 160 which communicate across a network, embodiments of the invention may be utilized with additional computers or fewer computers. For example, in one embodiment of the invention, a single computer may be utilized to process camera images and raise an alert when a cryogenic leak is detected. Optionally, images taken by the camera 130 may be received by a remote computer (e.g., an embedded computer system) and transmitted across a network 150 to the first computer 110 which then performs processing on the received images. The first computer 110 may then send a notification to the second computer 160 when a cryogenic leak is detected. In general, processing in the system may be performed by any suitable combination of computers located in any suitable locations.

Process for Detecting a Cryogenic Leak

In one embodiment of the invention, the I/R camera 130 may be used to capture an I/R image of an area of interest (e.g., an area in which cryogenic leaks may occur). Based on temperature measurements indicated by the I/R image, a determination may be made of whether a cryogenic leak has occurred within the area of interest. The determination may be made, for example, based on an absolute temperature measurement indicated by the I/R image (e.g., a cryogenic leak is detected where the absolute temperature in one or more array components of the I/R image is below a threshold temperature, e.g., below 0 degrees Celsius).

In some cases, such a threshold temperature may be used to distinguish between objects which are cold but do not leak and objects which have a cryogenic leak. For example, if the threshold temperature for identifying cryogenic leaks is 0 degrees Celsius (e.g., any array component or group of array components in an I/R image which has a temperature measurement which is below 0 degrees Celsius indicates that a cryogenic leak has occurred), then objects which are cooled to a temperature which is above 0 degrees Celsius (e.g., pipes with cryogenic liquefied gas flowing in them) but which do not have cryogenic leaks may not be identified as having cryogenic leaks. If such objects do develop leaks, causing the temperature of the object to fall below the threshold for cryogenic leak detections, then the leak may be detected and an alarm message may be generated.

In one embodiment, the determination may also be made based on a rate of temperature change of one or more array components over time (e.g., a cryogenic leak is detected where the rate of temperature change of a array component is greater than a threshold, e.g., where the temperature indicated by the array component is dropping faster than 5 degrees Celsius per second). Also, in some cases, the determination may be made using a combination of an absolute temperature threshold and a rate of change (e.g., a cryogenic leak is detected where either the temperature is below a threshold temperature value or where the rate of temperature change is greater than a threshold value, e.g., a cryogenic leak is detected if either the temperature of a array component is below 0 degrees Celsius or if the temperature of the array component is dropping faster than 5 degrees per second).

In some cases, the I/R camera 130 may be unable to distinguish between a range of certain low temperatures. For example, if the I/R camera 130 is only able to measure temperatures as low as a given minimum temperature (e.g., if the I/R camera 130 can only measure as low as −10 degrees Celsius), then the I/R camera 130 may be unable to distinguish between temperatures below the given minimum temperature (e.g., where the I/R camera 130 can only measure as low as −10 degrees Celsius, the I/R camera 130 may be unable to distinguish between −10 degrees Celsius and −100 degrees Celsius).

In some cases, where the I/R camera 130 cannot distinguish between a range of low temperatures, a portion of the objects within view of the I/R camera 103 may remain at a low temperature below the minimum measurable temperature, and as a result appear as cold spots in the I/R image. Such objects may be indistinguishable from a colder cryogenic leak (e.g., a cold pipe at −10 degrees Celsius may appear indistinguishable from a cryogenic leak at −100 degrees Celsius).

In one embodiment, where a selected threshold temperature for detecting cryogenic leaks is the minimum temperature measurable with the I/R camera 130 (e.g., where lower temperatures cannot be distinguished by the I/R camera 130 such that a lower threshold cannot be used), calibration of the I/R camera 130 may be used before determining whether a cryogenic leak has occurred. Such calibration may be used to identify objects which are below the minimum measurable temperature but which are also not indicative of a cryogenic leak (e.g., in the example provided above, such calibration may be used to identify the cold, non-leaking pipe at −10 degrees Celsius and subsequently distinguish the cold, non-leaking pipe from a cryogenic leak).

In one embodiment, the calibration may include recording an I/R image using the I/R camera 130 and determining one or more areas of the I/R image which are to be excluded for purposes of cryogenic leak detection. For example, an I/R image may be taken of an area of interest in which no cryogenic leaks are present (e.g., an area in which leaks may occur and which also contains the cold, non-leaking pipe described above). One or more areas within the I/R image which have temperatures at or below the minimum temperature measurable by the I/R camera 130 may then be identified (the areas may correspond, for example, to the cold, non-leaking pipe described above).

In one embodiment, the one or more areas of the I/R image which are identified may then be excluded during subsequent (i.e., after calibration) checking of subsequent I/R images for cryogenic leaks (e.g., the corresponding areas in subsequent I/R images captured by the I/R camera 130 may be ignored by the leak-checking algorithm). Thus, in the example described above, during subsequent leak detection, the cold, non-leaking pipe may not be identified as a cryogenic leak (e.g., because areas of the cold, non-leaking pipe are excluded during the leak detection process), while any other portion of the I/R image at or below the threshold temperature may be identified as a leak.

In one embodiment, such identification of one or more areas using calibration and subsequent exclusion of the one or more areas during a leak checking process may generally be used where a non-leaking object in the I/R camera view is to be excluded from leak-checking. For example, where the threshold temperature for leak detection is measurable by the I/R camera 130 and a non-leaking object falls below the threshold temperature, or where a threshold rate for temperature change is selected and a non-leaking object exhibits a temperature change above the threshold, areas in the I/R images corresponding to such non-leaking objects may be identified during calibration and excluded for purposes of leak detection.

Figure 2:
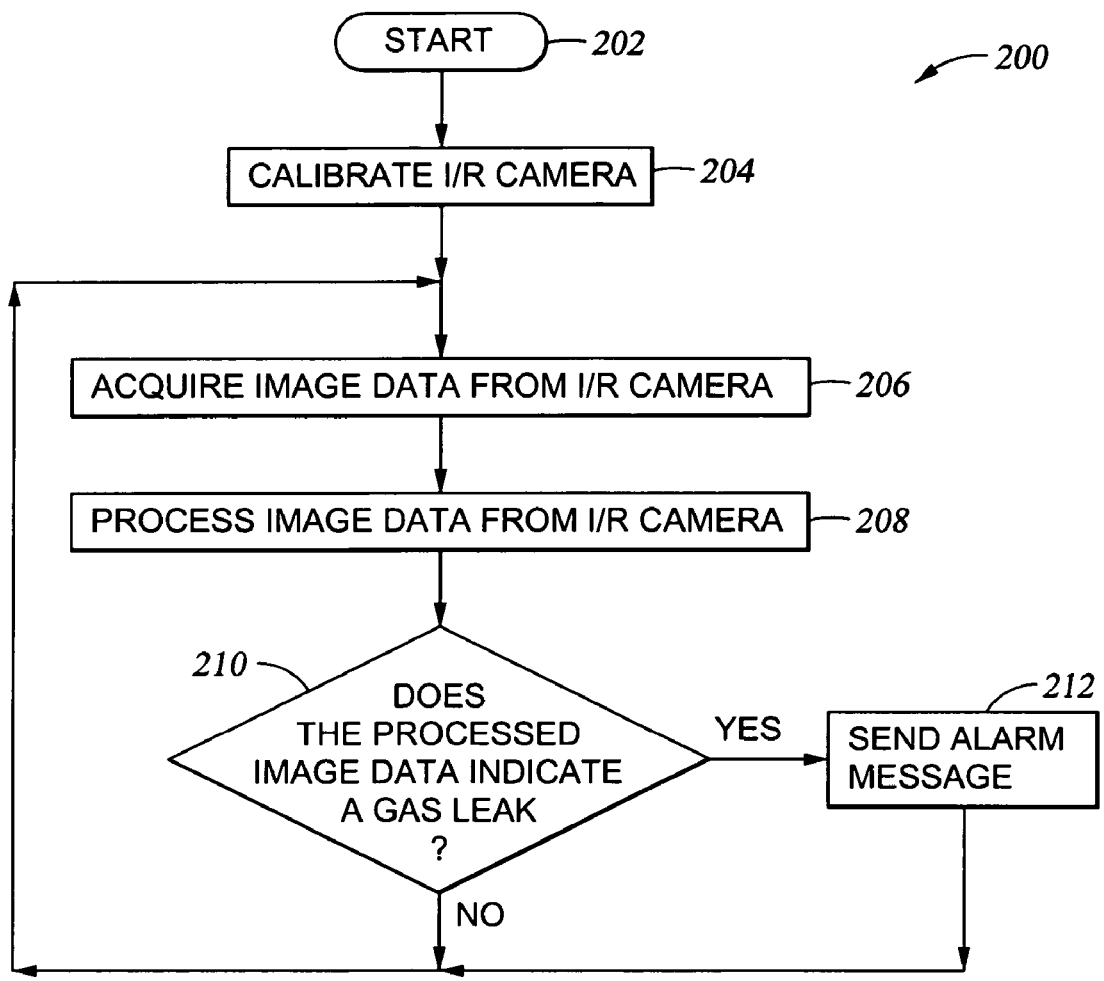
FIG. 2 is a flow diagram depicting a process for detecting a cryogenic leak according to one embodiment of the invention.

FIG. 2 is a flow diagram depicting a process 200 for detecting a cryogenic leak according to one embodiment of the invention. The process 200 may begin at step 202 and continue to step 204 where the I/R camera 130 is calibrated. As described below, the I/R camera 204 may be calibrated, for example, to avoid false-positives (e.g., situations in which the system 100 indicates that a cryogenic leak has been detected where no actual cryogenic leak has occurred). Such calibration may include, for example, determining one or more areas of an I/R camera image in which the measured temperature indicates a low temperature which is below the ambient temperature (e.g., a low temperature indicative of the presence of a cryogenic gas) but which does not correspond to a cryogenic leak. Such areas may include, for example, areas within the I/R image which are occupied by objects which are remain cold without leaking, such as an outlet pipe near a cryogenic gas storage tank. The one or more areas may correspond, for example, to individual array components of the I/R camera image.

At step 206, an I/R image may be acquired from the I/R camera 130. Such acquisition may include, for example, send a request to the I/R camera 130 and receiving a response from the I/R camera 130 which includes data for the I/R image acquired by the I/R camera 130.

At step 208, the I/R image data from the I/R camera 208 may be processed, for example, to extract temperature information within the I/R image. In some cases, such processing may include merely reading the I/R image from the I/R camera 130 into a data structure or file which provides a suitable format of the I/R image for subsequent processing.

At step 210, a determination may be made of whether the processed I/R image data indicates a cryogenic leak. Such processing may include, for example, determining whether one or more array components of the I/R image indicate a low temperature below the ambient temperature and indicative of a cryogenic leak. Such a determination may exclude the one or more areas identified above during the calibration step 204 of the process 200 (e.g., array components which indicate a low temperature below the ambient temperature but which do not correspond to a cryogenic leak). If a cryogenic leak is detected, an alarm message may be sent 212, e.g., to a computer 160 which notifies a user of the cryogenic leak. The process 200 may continue monitoring for cryogenic leaks at step 206.

Exemplary Cryogenic Leak Detection Arrangement

Figure 3:
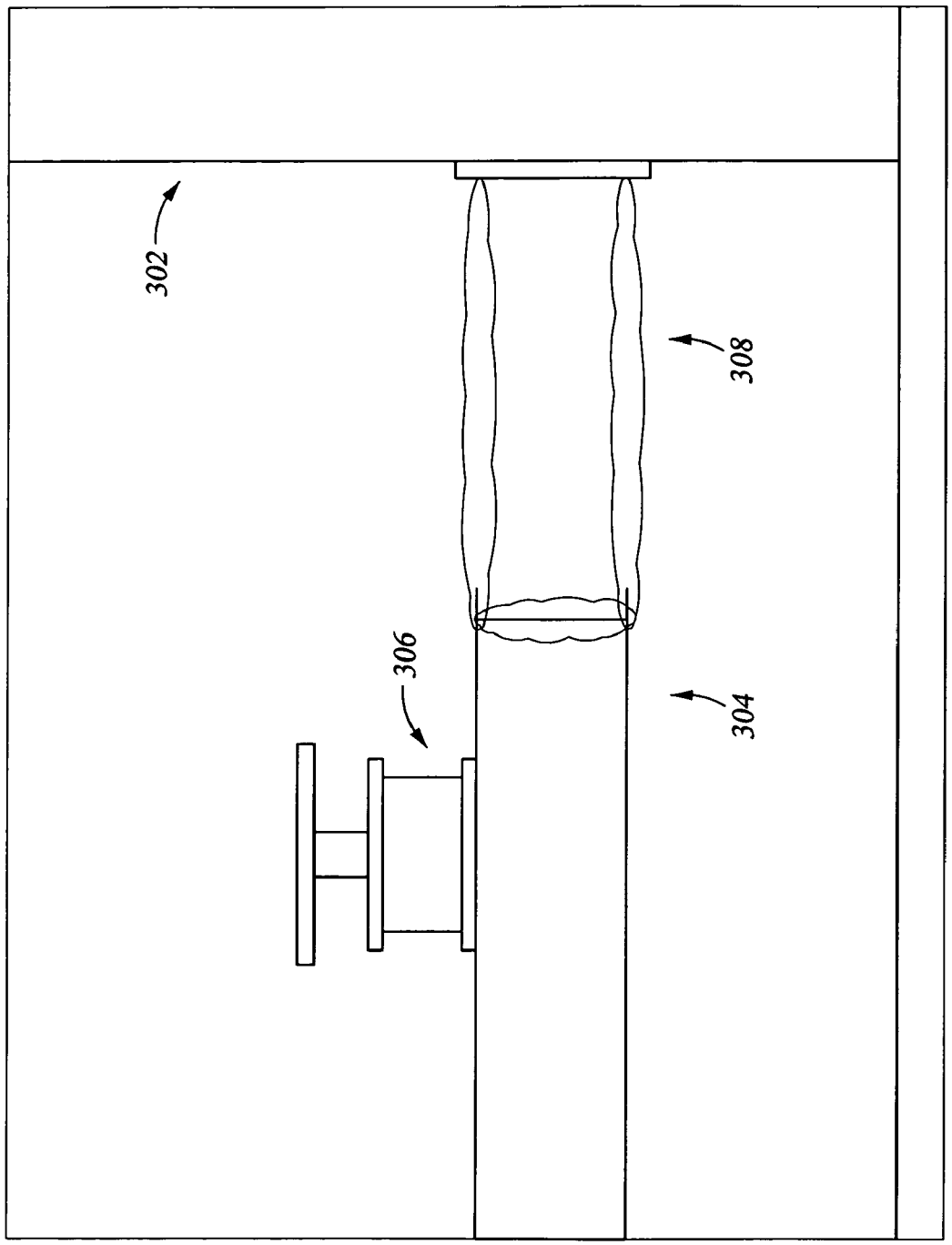
FIG. 3 is a block diagram depicting a gas line connected to a storage tank according to one embodiment of the invention.

An exemplary cryogenic leak detection arrangement provided by the system 100 is now described with respect to FIGS. 3-8. FIG. 3 is a block diagram depicting a liquefied cryogenic gas line 304 connected to a storage tank 302 according to one embodiment of the invention. The storage tank 302 may be used to store a liquefied cryogenic gas or liquid such as liquid oxygen (LOX) or liquid nitrogen (LIN). As depicted, the liquefied cryogenic gas line 304 may include a valve 306. Also, due to the liquefied cryogenic gas stored in the storage tank 302, a section 308 of the liquefied cryogenic gas line 304 may be cooled (as indicated by the frost covering the cooled section 308).

Figure 4:
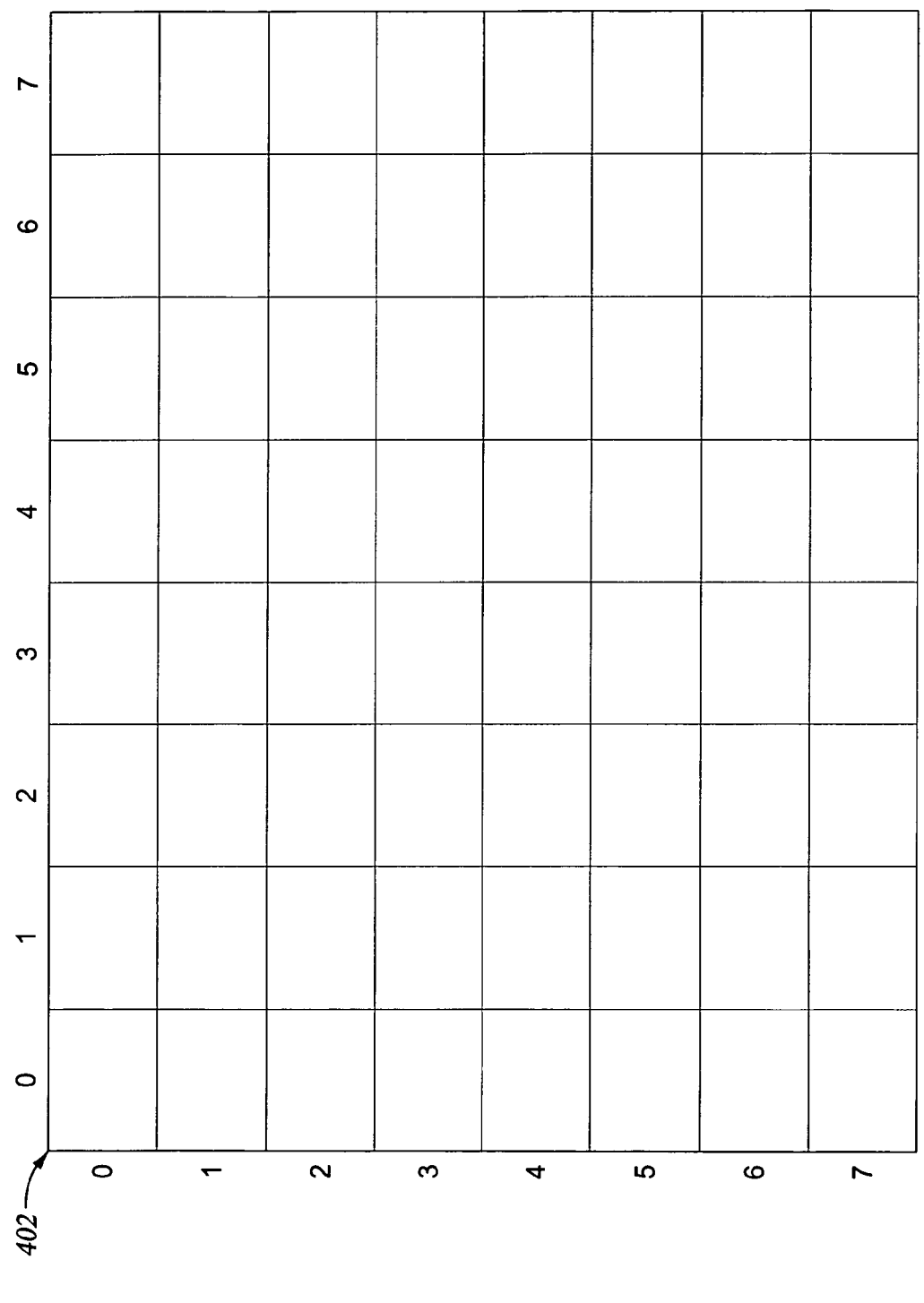
FIG. 4 is a block diagram depicting the temperature array of an infrared (I/R) camera according to one embodiment of the invention.

As described above, an I/R camera 130 may be used to determine if a cryogenic leak occurs. The I/R camera 130 may provide I/R images in which each array component indicates a temperature of the portion of the image covered by the array component. FIG. 4 is a block diagram depicting an I/R image 400 of an infrared (I/R) camera including a plurality of array components 402 according to one embodiment of the invention.

In one embodiment of the invention, the I/R camera 130 may be directed at portions of a plant or pipeline in which cryogenic leaks tend to occur. For example, I/R cameras 130 may be provided which monitor air separation units (ASUs) at areas including any storage system such as a storage tank 302, storage containers, at areas including any delivery system such as pipelines or vessels, and/or at areas including any transformation system such as valves or pumps. Thus, as depicted in FIG. 5, the I/R camera 130 may be directed at the storage tank 302, liquefied cryogenic gas line 304, and the valve 306.

As described above, the I/R camera 130 may be calibrated before the system 100 uses the I/R camera 130 to determine if a cryogenic leak has occurred. During calibration, a determination may first be made that no leaks currently exist in the area being viewed using the I/R camera 130. By ensuring that no leaks currently exist, a determination may be made of which areas being viewed using the I/R camera 130 have a low temperature which is lower than the ambient temperature and indicative of the presence of a liquefied cryogenic gas.

Such a determination may be made, for example, by visual inspection prior to calibration (e.g., by an operator of the system 100) or by referring to previous calibrations (e.g., previous I/R images which indicate expected temperatures in the environment being monitored which are not indicative of cryogenic leaks).

Figure 5:
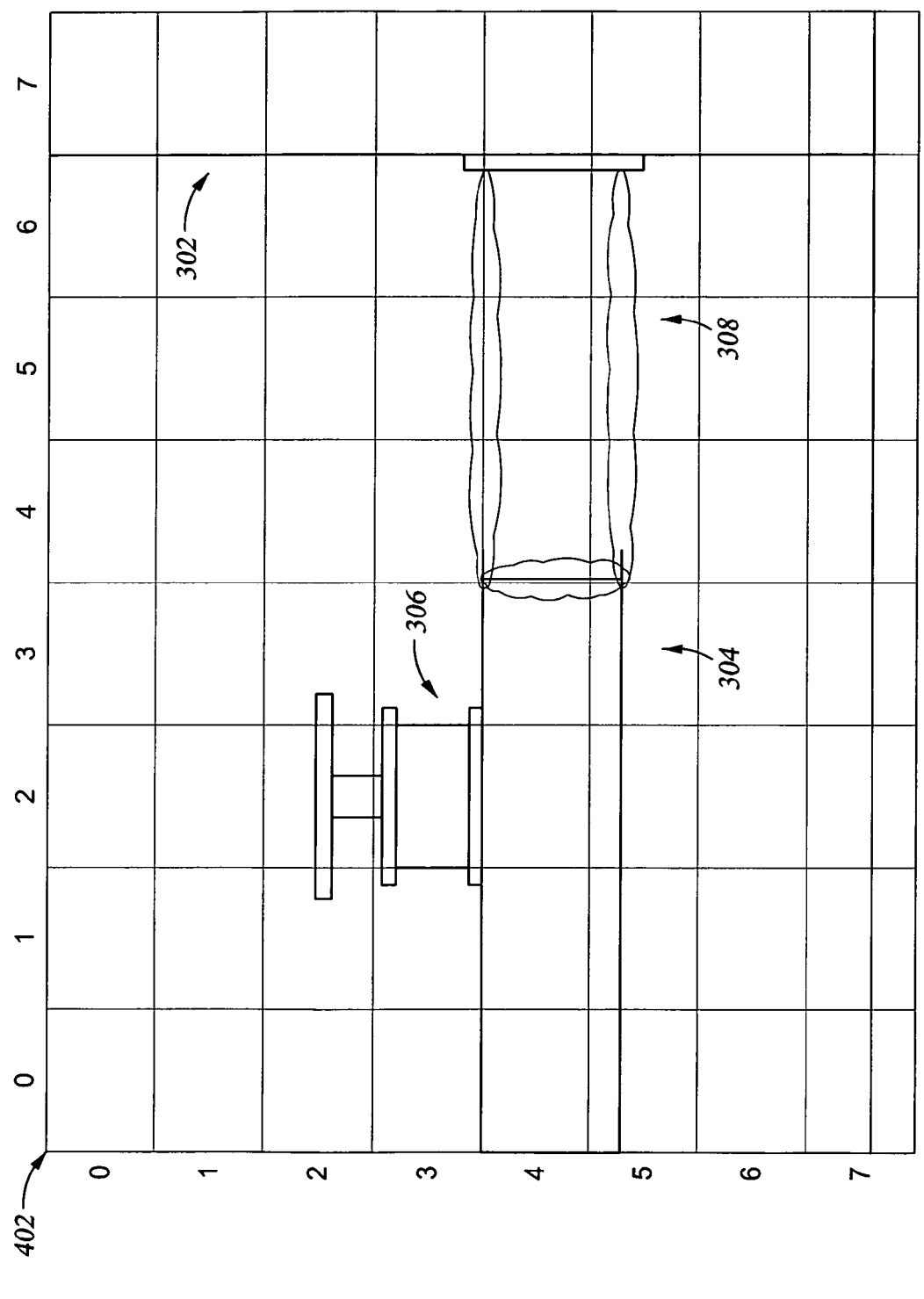
FIG. 5 is a block diagram depicting a gas line connected to a storage tank overlaid by the temperature array of an I/R camera according to one embodiment of the invention.

As an example of calibration, as depicted in FIG. 5, no leaks are present around the storage tank 302, gas line 304, or valve 306, but the gas line 304 may have a low temperature below the ambient temperature in area 308, corresponding to array components (5, 4), (6, 4) and a portion of array components (5, 5), (6, 5) (array component values given herein are provided in (x, y) location format). The area 308 may not be indicative of a leak, but may merely reflect expected cooling of the gas line 304 near its connection to the storage tank 302.

Figure 6:
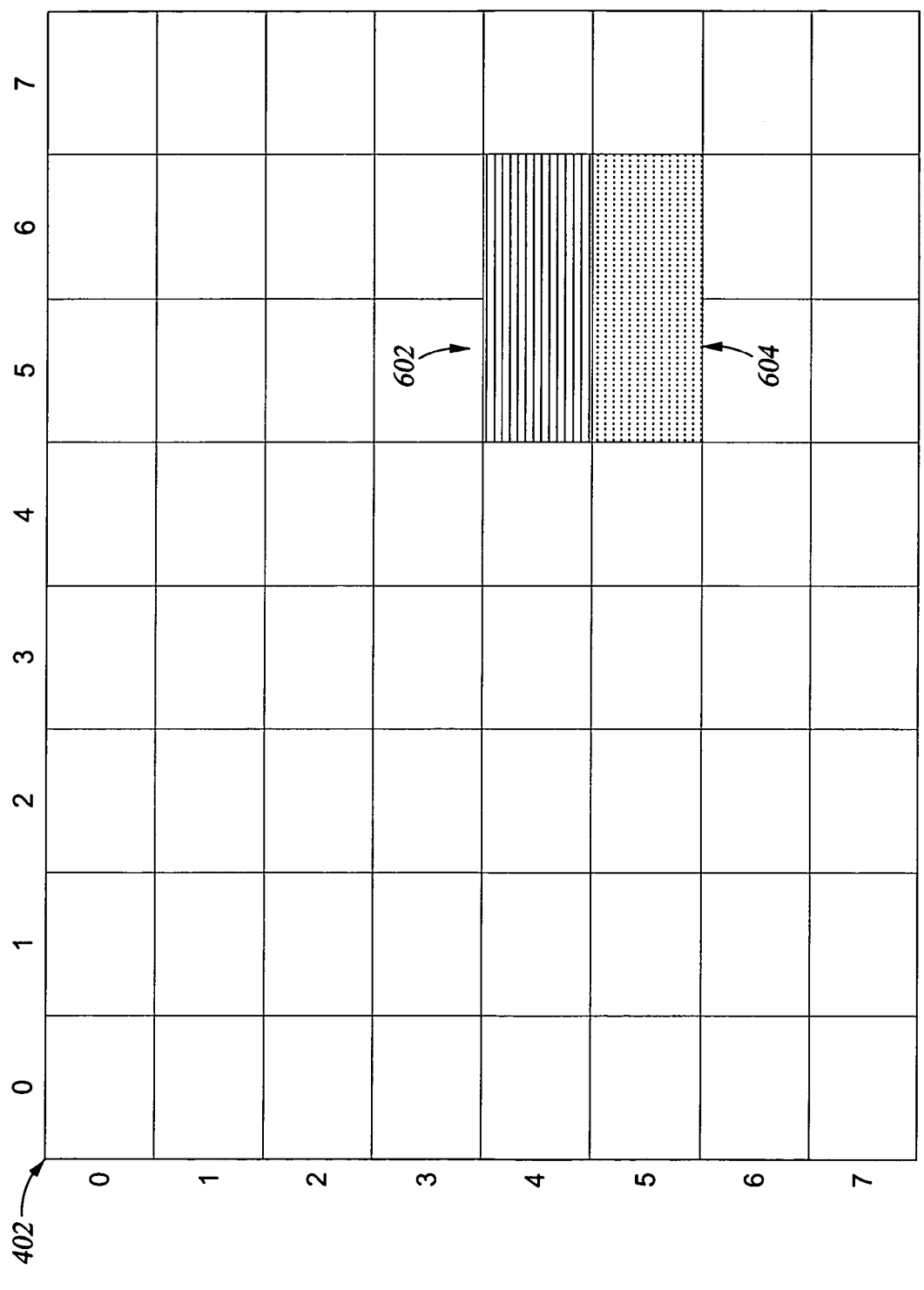
FIG. 6 is a block diagram depicting an I/R camera image of a gas line connected to a storage tank according to one embodiment of the invention.

Thus, as depicted in the I/R image 600 of FIG. 6, one area 602 of the I/R image 600 may indicate a first low temperature and another area 604 of the I/R image 600 may indicate a second low temperature. The first area 602 may indicate a lower temperature 602 than the second area 604 because the aggregate temperature of the objects occupying the array components in the area 602 (the array components in area 602 are entirely occupied by the cooled area 308 of the gas line 304) is lower than the aggregate temperature of the objects occupying the array components in area 604 (the array components in area 604 are only partially occupied by the cooled area 308 of the gas line 304). During calibration, the location of the areas 602, 604 (e.g., the array component locations and/or the temperatures at those array component locations) may be recorded for future reference. For example, such areas 602, 604 may be excluded (or otherwise accounted for) during future detection of cryogenic leaks (e.g., such areas 602, 604 of low temperature may not cause an alarm message to be generated).

Figure 7:
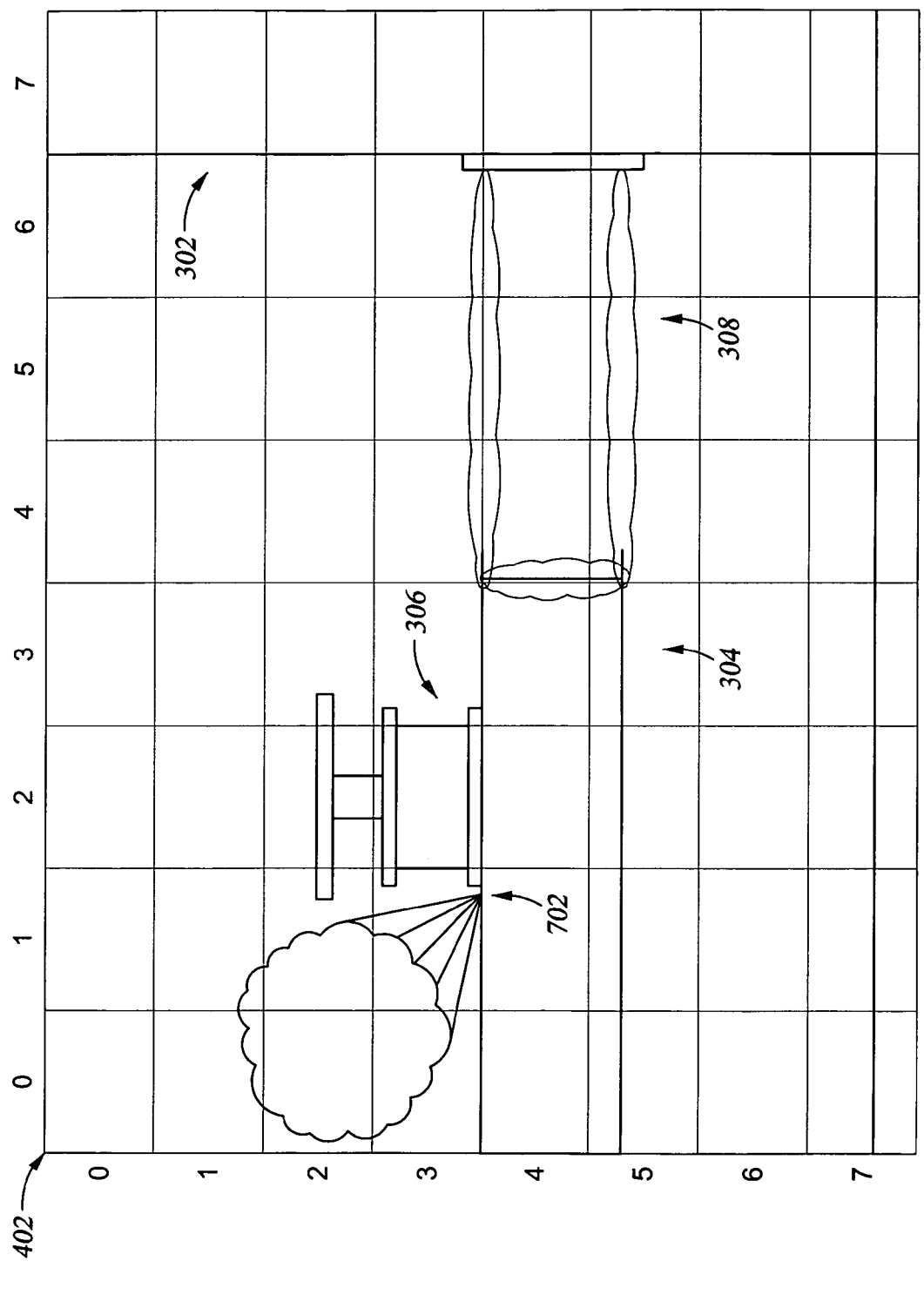
FIG. 7 is a block diagram depicting a cryogenic leak according to one embodiment of the invention.

After the I/R camera 130 has been calibrated, the I/R camera 130 may be utilized to detect a cryogenic leak. FIG. 7 is a block diagram depicting a cryogenic leak 702 according to one embodiment of the invention. As depicted, the leak 702 is located at the connection between the valve 306 and the gas line 304. When a leak 702 occurs, when the cryogenic liquefied gas contacting warmer air may cause the cryogenic liquid to rapidly vaporize, thereby forming a vapor cloud. As a result, the vapor cloud may lower the ambient temperature in the vicinity of the cloud. As depicted, the vapor cloud fills an area covered by array components (0, 2), (1, 2), (0, 3), and (1, 3).

Figure 8:
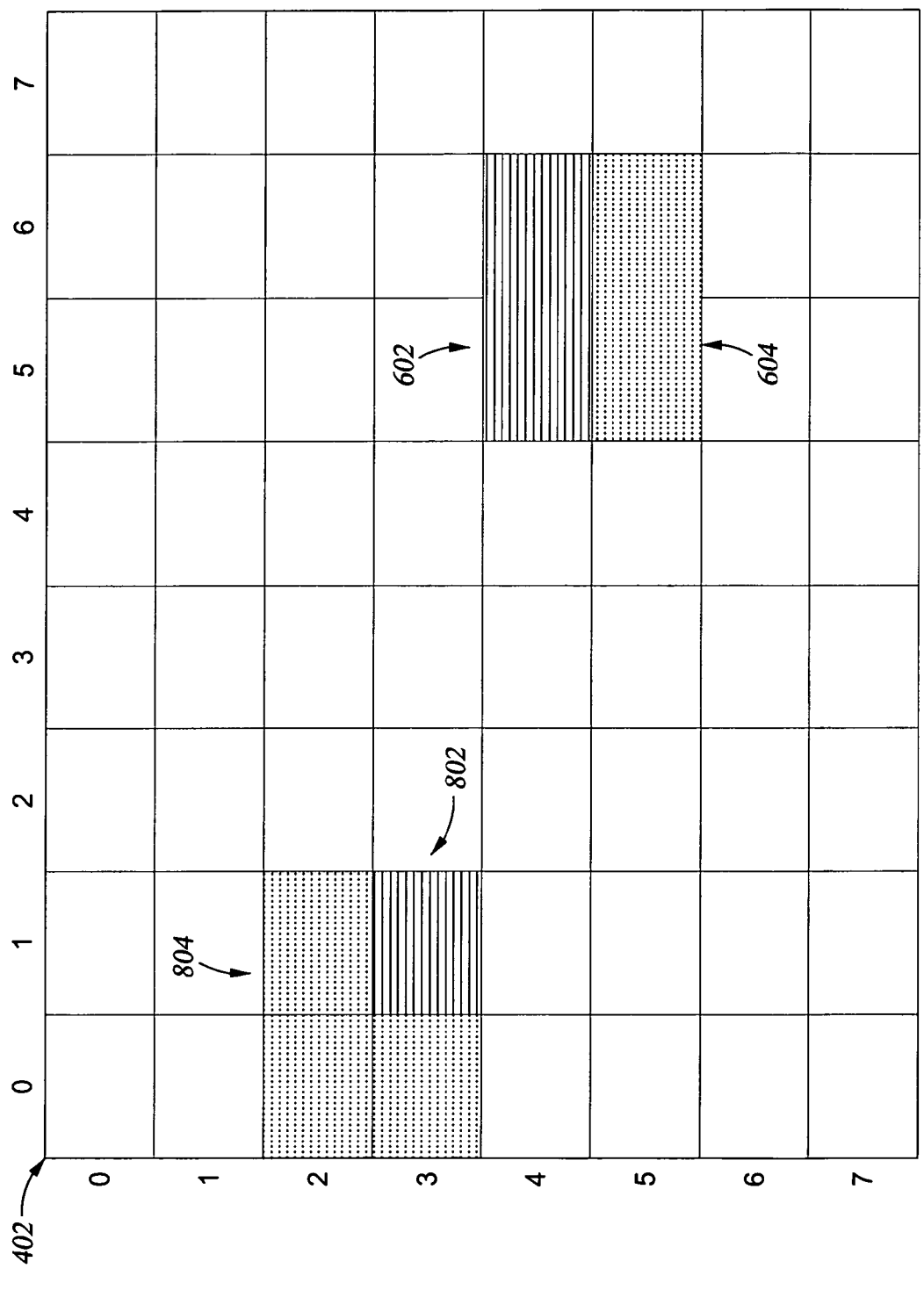
FIG. 8 is a block diagram depicting an I/R camera image of a cryogenic leak according to one embodiment of the invention.

As described above, the I/R camera 130 may capture an I/R image of the vapor cloud caused by the leak 702. By detecting one or more array components which indicate a temperature lower than the ambient temperature, the first computer 110 may determine that the cryogenic leak 702 has occurred. FIG. 8 is a block diagram depicting an I/R camera image 800 of a cryogenic leak 702 according to one embodiment of the invention. As depicted, the I/R image 800 may include the areas 602, 604 identified during calibration. As described above, such areas 602, 604 may be ignored in determining whether to signal an alarm because the low temperature in those areas 602, 604 may be expected (e.g., a low temperature may be expected between the storage tank 302 and the gas line 304) and may not be indicative of a cryogenic leak 702.

With respect to the cryogenic leak 702, the I/R camera 130 may detect the cryogenic leak 702 as areas 802, 804 of low temperature (e.g., a low temperature below the ambient temperature) which were not identified during calibration of the I/R camera 130. Such a determination may be made, for example, by comparing an I/R image 600 received during calibration of the I/R camera 130 with the present image 800 received from the I/R camera 130. When the comparison indicates the new areas 802, 804 of low temperature which are indicative of a leak 702, the first computer 110, for example, may send an alarm message to the second computer 160, thereby causing a notification 172 regarding the leak 702 to be displayed to the user of the second computer 160 as described above. Thus, the cryogenic leak 702 may be detected as soon as the leak 702 occurs, providing an alarm message quickly and allowing the user of the second computer system 160 to be notified.

In some cases, absolute temperatures of a portion of the I/R image 800 may not be used to determine if a leak 702 has occurred. For example, in one embodiment of the invention, the I/R camera 130 may be used to detect a sudden drop in temperature (e.g., a drop in temperature which is above a threshold value for temperature change for a specified amount of time) which is indicative of a cryogenic leak 702. Where a drop in temperature is used to determine whether a cryogenic leak 702 has occurred, an I/R camera 130 with a sufficient sampling rate may be used to detect the specified temperature change in the specified amount of time. For example, if the threshold for leak detection is a 10 degree Celsius drop in temperature over 2 seconds, the selected I/R camera 130 may be capable of detecting a temperature change of +/−5 degrees Celsius/second.

In some cases, a leakage may cause the outer walls of any device that contains cryogenic liquefied gas to reach a thermal equilibrium with a low temperature which is below the ambient temperature. Thus, the I/R camera 130 may also be used to detect leaks by measuring the temperature of the outer walls of devices containing cryogenic liquefied gas to determine if a leak 702 has occurred. The difference between the ambient temperature and the surface temperature due to the cryogenic leak may also be increased due to insulation material covering the outer walls of the device. The insulation may reduce conductive heat transfer from areas at the ambient temperature to areas affected by the cryogenic leak 702, thereby increasing contrast between the areas affected by the leak 702 and areas at the ambient temperature. The increased contrast may make detection of a cryogenic leak 702 more effective, e.g., by providing a clearer I/R image 800 of the leak 702. Also, in one embodiment, surfaces which the I/R camera 130 is monitoring (e.g., the surface of the storage tank 302 and/or the surface of the gas line 304) may be painted with a coat of paint with a low thermal conductivity which may reduce noise from the background of the I/R image 800 and thereby provide a better estimation of the size of the leak.

Selection of the I/R Camera

In one embodiment of the invention, the I/R camera 130 may be selected based on several considerations such as the temperature range measurable using the camera, the resolution of the camera, the accuracy of the camera in measuring a temperature, the capture rate of the camera, the wavelength of the measured radiation for the camera, and the image transfer and connectivity capabilities of the camera.

For example, while described above with respect to an I/R camera 130 with relatively low resolution (e.g., 16×16), other cameras may be utilized with higher resolutions (e.g., 320×240). In some cases, the selected I/R camera 130 may also provide sensitive measurements, for example, which allow detection of a +/−2% temperature change or a +/−2 degree Celsius change for each array component in an I/R image. Optionally, the camera 130 may provide a degree of measurement sensitivity above a selected threshold for sensitivity.

In one embodiment of the invention, the I/R camera 130 may provide a frame rate which is sufficient to detect a sudden change in temperature indicative of a cryogenic leak 702. For example, if the camera 130 is used to monitor an environment in which the cryogenic material subject to leakage dissipates quickly (e.g., in a warm environment in which the leaking material quickly evaporates), an I/R camera 130 with a sampling rate above a threshold frame rate may be selected. For example, an I/R camera 130 may be selected which provides a capture rate of 7 frames/second to 120 frames/second.

In one embodiment of the invention, the camera 130 may be selected to detect an appropriate wavelength of I/R radiation. For example, the camera 130 may be selected to measure both long wave (e.g., 8-15 micron) and/or short wave (e.g., 2-6 micron) type I/R radiation. In one embodiment, the camera 130 may detect a wavelength greater than 14 microns. In one embodiment, the I/R camera 130 may, for example, be an IRI 1001E (r) camera manufactured by IRISYS, Inc.

In one embodiment of the invention, the I/R camera 130 may utilize one of a photoconductive detector, a photovoltaic detector, and a microbolometer detector to obtain I/R images. Where a photoconductive detector is used, an electric potential may be applied across an absorbing region of the detector and cause a current to flow in proportion to the irradiance if photon energy from the I/R radiation exceeds the energy gap between the valence and the conduction band. Photoconductive detectors may include photoconductive detectors for the visible wavelength range e.g. cadmium sulfide (CdS) photoconductive detectors, photoconductive detectors for the near infrared wavelength range e.g. lead sulfide (PbS) photoconductive detectors, photoconductive detectors for the infrared wavelength range e.g. silicon doped with arsenide (Si:As) photoconductive detectors, and the mercury-cadmium-telluride (HgCdTe) photoconductive detector.

In one embodiment, where a photovoltaic detectors is used, the detector may generate an electrical output proportional to the illumination of a junction of two different materials or of a junction of similar materials containing different impurities within the detector. Typical materials may include combinations of iron and selenium or copper and copper oxide. Other materials may include silicon, germanium, indium arsenide, and indium antimonide. Doping of different parts of the material may be used to form a light-sensitive p-n junction within the detector. In a homo-junction detector, the p-layer within the detector may be exposed to incident I/R radiation and, in response, produce electrical charges. In a heterojunction detector, the detector may utilize a combination of dissimilar materials, for instance, glass and crystal silicon, nGe—nSi, pCu2S—nCdS, pSi—nCdS, and other compounds. The photovoltaic detector may contain a thin layer of a p-type material exposed to light. This layer may form a junction with a more massive, n-type material of the semiconductor. The p-type and n-type material surfaces may be provided with plated metal electrodes and solder terminals for connecting leads.

In one embodiment of the invention, the photovoltaic and photoconductive detectors, where used, may operate at a low temperature and use cryogenic refrigeration units to achieve, for example, −200 degree Celsius operating temperatures. To maintain such temperatures, the detector may be enclosed in a vacuum housing such as a Dewar with a suitable window transparent at the required I/R wavelengths being measured.

In one embodiment, where a microbolometer detector is utilized, the electrical resistivity of the detector material may change with temperature and produce high-resolution images without requiring cryogenic cooling. The increased resolution in a microbolometer detector may allow the detection of tiny temperature variations.

In one embodiment, the selected I/R camera 130 may not measure the actual temperature of a cryogenic leak 702. For example, the temperature of the cryogenic leak 702 may be so low that the I/R camera is incapable of correctly measuring the temperature. In such cases, instead of determining an absolute temperature measured by the I/R camera 130, the I/R camera 130 may merely be used to determine an area in which the temperature indicated by the I/R image is lower than the ambient temperature of the environment viewed using the I/R camera 130. Such an area may be indicative of the cryogenic leak 702 and therefore be used to detect the leak 702.

Also, in some cases, where the I/R camera 130 does not measure the actual temperature of the cryogenic leak, the I/R camera 130 may be selected such that the lowest temperature that the I/R camera 130 is capable of detecting is lower than the lowest ambient temperature of the environment being viewed using the I/R camera 130. For example, in cold environments close to the artic in the northern hemisphere, the ambient temperature may reach extreme low temperatures which are not reached closer to the equator. In order to distinguish between a cryogenic leak 702 and the low ambient temperature of such environments, an I/R camera 130 may be selected which is capable of distinguishing between a low ambient temperature and a lower temperature of a cryogenic leak 702. For example, the I/R camera 130 may be capable of measuring temperatures lower than a record low temperature for the environment which the I/R camera 130 is used to monitor.

In one embodiment, the camera 130 may provide multiple camera settings which may be modified, e.g., using the first computer 110. For example, the camera 130 may provide higher resolution settings, user-selectable sensitivity settings, user selectable temperature measurement ranges, automatic adjustments for sensitivity and range settings, and different display palettes such as red/blue palettes, green/blue palettes, and grayscale palettes. The camera 130 may also provide multiple moveable temperature measurement cursors for measuring the temperature at various array components in an image, user-selectable emissivity values, user-selectable image integration, for example, of one to ten frames, read-out/in in degrees Celsius and/or degrees Kelvin and other image manipulation settings.

In one embodiment, the camera 130 may also be utilized with software which may, for example, provide real-time image and temperature measurement display. Such software may also provide multiple image storage and retrieval, time and temperature display for up to ten user defined array components, the ability to save all array component temperature values to a spreadsheet, such as, for example, a Microsoft Excel(r) spreadsheet, the ability to cut and paste images into other Microsoft applications, and/or reflected ambient temperature compensation.

Calibration of the System

As described above, the system 100 may be calibrated before operation to ensure that the first computer 110 does not incorrectly indicate that a cryogenic leak 702 has occurred. The calibration may include detecting and subsequently ignoring one or more low-temperature areas monitored by the I/R camera 130 which do not correspond to cryogenic leaks 702. In one embodiment, the calibration may be performed at a single time, e.g., before operation of the I/R camera 130 and/or before operation of the leak detection program 118 of the first computer system 110 is initiated. Optionally, the calibration may be performed periodically (e.g., the calibration may be performed once a minute). Such periodic calibration may be used, for example, to prevent slight changes in the environment monitored by the I/R camera 130 from indicating that a non-existent leak has occurred. For example, if the sun is shining on an area during calibration of the I/R camera 130, when the sun subsequently sets, the area may cool several degrees. Such cooling may occur over the course of several hours as the sun goes down and is not indicative of a leak in the area which the sun was shining on. By periodically calibrating the I/R camera 130, the slow change in temperature of the area affected by the sun may appropriately ignored by the leak detection program 118.

In one embodiment, a user may be able to select regions of interest which are monitored for cryogenic leaks 702 while other regions outside of the regions of interest may be ignored. For example, with respect to FIG. 6, a user may indicate that the low temperature of areas 602, 604 is to be ignored during operation of the leak detection system 100. The user may make the indication, for example, by selecting the array components in the areas 602, 604 to be ignored. Such a selection may be made, for example, by manually indicating the array components or by using a mouse or other input device to trace a region of the I/R image in which temperature changes are to be ignored.

In one embodiment of the invention, a rotating I/R camera 130 may be utilized, for example, to monitor a larger portion of an area of interest. Where a rotating I/R camera 130 is utilized, the camera 130 may be calibrated at several positions during the rotation and images captured at those positions may be used to determine if a cryogenic leak 702 has occurred. For example, if the I/R camera 130 rotates 180 degrees, calibration of the camera 130 may be performed when the camera has rotated 0 degrees, 60 degrees, 120 degrees, and 180 degrees. Each of the I/R images captured during calibration may be used for comparison to subsequent I/R images taken when the camera has rotated 0 degrees, 60 degrees, 120 degrees, and 180 degrees. If the comparison for any of the I/R images indicates a new area of low temperature where the low temperature is significantly lower than the ambient temperature, then the leak detection program 118 may indicate that a cryogenic leak 702 has occurred.

Image Processing of the I/R Images

As described above, in one embodiment of the invention, I/R images received from the I/R camera 130 may be processed during the process of leak detection. Image processing performed on the I/R images may include filtering, segmentation and edge detection, and 3D/2D profiling. Filtering may be utilized to remove various noise signals from the I/R images (e.g., statistical noise such as Poisson noise) and thereby increase the accuracy of temperature measurement with respect to the images.

In one embodiment, segmentation and edge detection algorithms may be used to detect the area of a leak 702 and estimate the severity of the leak 702. Segmentation and edge detection may also be used during calibration to identify areas 602, 604 which may have a lowered temperature but which may not be indicative of a leak 702.

In one embodiment, where 3D/2D profiling is utilized, a 360 degree scan may be performed of the area of interest to estimate the 3D and 2D profile of the temperature distribution of the area monitored by the I/R camera 130. The 3D and 2D profiles may then be used to detect the presence of a leak 702, e.g., by detecting a change in temperature of an area of the 2D profile or by detecting a change in temperature of a volume of the 3D profile. Also, in some cases, image processing software may also be utilized to convert the I/R images into an appropriate format, e.g., TIFF or BMP, to allow the image to be processed by standard software such as VC++(r), MAT LAB (r), LAB VIEW (r), or other appropriate software.

Leak Detection using the I/R Images

In one embodiment of the invention, the I/R images received from the I/R camera 130 may be used to determining a cryogenic leak 702 has occurred. As described above, such a determination may include determining a change in temperature in a portion of an I/R image. In some cases, advanced computational models such as machine learning may be used to enhance detection of cryogenic leaks using the received I/R images and to reduce false-positives produced by the system 100. Such models may include adaptive machine learning algorithms such as Back-Propagation Feed-Forward Neural Networks, Expectation Maximization (EM) algorithms, etc.

CONCLUSION

Thus, as described above, embodiments of the invention provide a method, article of manufacture, and system of detecting a cryogenic leak. In one embodiment, the method includes calibrating an infrared camera by detecting one or more first areas of low temperature in a first infrared image of a location received from the infrared camera wherein the low temperature is lower than an ambient temperature, detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas, and in response to detecting the one or more second areas of low temperature in the second infrared image, generating an alarm message which indicates the cryogenic leak. By utilizing an infrared image to detect the cryogenic leak, a more accurate detection of the cryogenic leak may be provided, e.g., by detecting regions of the infrared image affected by the cryogenic leak.

Preferred processes and apparatus for practicing the present invention have been described. It will be understood and readily apparent to the skilled artisan that many changes and modifications may be made to the above-described embodiments without departing from the spirit and the scope of the present invention. The foregoing is illustrative only and that other embodiments of the integrated processes and apparatus may be employed without departing from the true scope of the invention defined in the following claims.

What is claimed is:

1. A method of detecting a cryogenic leak comprising:
   a) calibrating an infrared camera by detecting one or more first areas of low temperature in a first infrared image of a location received from the infrared camera wherein the low temperature is lower than an ambient temperature;
   b) detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas; and
   c) in response to detecting the one or more second areas of low temperature in the second infrared image, generating an alarm message which indicates the cryogenic leak.

2. The method of claim 1, wherein the one or more first areas include one or more first array components and wherein the one or more second areas include one or more second array components.

3. The method of claim 1, wherein the alarm message is generated only if a rate of decrease of temperature of the one or more second areas of low temperature is above a threshold rate corresponding to the cryogenic leak.

4. The method of claim 1, further comprising:
   d) sending the alarm message across a network to a computer, wherein the alarm message includes one of the second infrared image and a description of a location of the cryogenic leak.

5. The method of claim 1, further comprising:
   d) processing the second infrared image using an edge-detection algorithm to determine the one or more second areas of low temperature.

6. The method of claim 1, further comprising:
   d) processing the second infrared image using a noise filter to remove noise in the second infrared image.

7. The method of claim 1, further comprising:
   d) receiving a user selection of one or more third areas in a third infrared image of the location; and
   e) preventing detection of a temperature change within the one or more third areas during detection of the one or more second areas of low temperature.

8. The method of claim 1, wherein the infrared camera is configured to detect a low temperature which is lower than a lowest recorded ambient temperature of the location.

9. A computer-readable medium including a program which, when executed by a processor, performs a method of detecting a cryogenic leak, the method comprising:
   a) calibrating an infrared camera by detecting one or more first areas of low temperature in a first infrared image of a location received from the infrared camera wherein the low temperature is lower than an ambient temperature;
   b) detecting one or more second areas of low temperature in a second infrared image of the location received from the infrared camera wherein the low temperature in the second infrared image is lower than the ambient temperature and indicative of the cryogenic leak, and wherein the one or more second areas are not the one or more first areas; and
   c) in response to detecting the one or more second areas of low temperature in the second infrared image, generating an alarm message which indicates the cryogenic leak.

10. The computer-readable medium of claim 9, wherein the one or more first areas include one or more first array components and wherein the one or more second areas include one or more second array components.

11. The computer-readable medium of claim 9, wherein the alarm message is generated only if a rate of decrease of temperature of the one or more second areas of low temperature is above a threshold rate corresponding to the cryogenic leak.

12. The computer-readable medium of claim 9, wherein the method further comprises:
   d) sending the alarm message across a network to a computer, wherein the alarm message includes one of the second infrared image and a description of a location of the cryogenic leak.

13. The computer-readable medium of claim 9, wherein the method further comprises:
   d) processing the second infrared image using an edge-detection algorithm to determine the one or more second areas of low temperature.

14. The computer-readable medium of claim 9, wherein the method further comprises:
   d) processing the second infrared image using a noise filter to remove noise in the second infrared image.

15. The computer-readable medium of claim 9, wherein the method further comprises:
   d) receiving a user selection of one or more third areas in a third infrared image of the location; and
   e) preventing detection of a temperature change within the one or more third areas during detection of the one or more second areas of low temperature.

16. The computer-readable medium of claim 9, wherein the infrared camera is configured to detect a low temperature which is lower than a lowest recorded ambient temperature of the location.

17. A system comprising:

a) an infrared camera; and b) a processor configured to:
  i) calibrate the infrared camera by detecting one or more first areas of low temperature in a first infrared image of a location received from the infrared camera wherein the low temperature is lower than an ambient temperature;
  ii) detect one or more second areas of low temperature in a second infrared image of the location received from the infrared camera wherein the low temperature in the second infrared image is lower than the ambient temperature and indicative of the cryogenic leak, and wherein the one or more second areas are not the one or more first areas; and
  iii) in response to detecting the one or more second areas of low temperature in the second infrared image, generate an alarm message which indicates the cryogenic leak.

18. The system of claim 17, wherein the one or more first areas include one or more first array components and wherein the one or more second areas include one or more second array components.

19. The system of claim 17, wherein the alarm message is generated only if a rate of decrease of temperature of the one or more second areas of low temperature is above a threshold rate corresponding to the cryogenic leak.

20. The system of claim 17, wherein the processor is further configured to:
  iv) send the alarm message across a network to a computer, wherein the alarm message includes one of the second infrared image and a description of a location of the cryogenic leak.

21. The system of claim 17, wherein the processor is further configured to:
  iv) process the second infrared image using an edge-detection algorithm to determine the one or more second areas of low temperature.

22. The system of claim 17, wherein the processor is further configured to:
  iv) process the second infrared image using a noise filter to remove noise in the second infrared image.

23. The system of claim 17, wherein the processor is further configured to:
  iv) receive a user selection of one or more third areas in a third infrared image of the location; and
  v) prevent detection of a temperature change within the one or more third areas during detection of the one or more second areas of low temperature.

24. The system of claim 17, wherein the infrared camera is configured to detect a low temperature which is lower than a lowest recorded ambient temperature of the location.

25. The system of claim 17, wherein one or more surfaces of the location monitored by the infrared camera are painted with a paint having low thermal conductivity.

* * * * *